United States Patent [19]

Gregory et al.

[11] Patent Number: 4,599,470

[45] Date of Patent: Jul. 8, 1986

[54] PROCESS FOR THE TRANSALKYLATION OR DEALKYLATION OF ALKYL AROMATIC HYDROCARBONS

[75] Inventors: Reginald Gregory, Camberley; David J. Westlake, Woking, both of England

[73] Assignee: The British Petroleum Company P.L.C., London, England

[21] Appl. No.: 551,862

[22] Filed: Nov. 15, 1983

[30] Foreign Application Priority Data

Nov. 18, 1982 [GB] United Kingdom .................. 8232992

[51] Int. Cl.$^4$ .............................................. C07C 5/22
[52] U.S. Cl. .................................... 585/323; 585/474; 585/475; 585/486
[58] Field of Search ................ 585/474, 475, 486, 323

[56] References Cited

U.S. PATENT DOCUMENTS

| | | | |
|---|---|---|---|
| 2,222,632 | 11/1940 | Sachanen et al. | 585/474 |
| 2,930,820 | 3/1960 | Aries | 585/474 |
| 3,268,607 | 8/1966 | Schmitt et al. | 585/474 |
| 4,238,364 | 12/1980 | Shabtai | 502/65 |
| 4,248,739 | 2/1981 | Vaughan et al. | 502/63 |

*Primary Examiner*—Curtis R. Davis
*Attorney, Agent, or Firm*—Brooks, Haidt, Haffner & Delahunty

[57] ABSTRACT

Alkyl aromatic hydrocarbons wherein the alkyl group is a $C_1$ to $C_{10}$ alkyl group are transalkylated or dealkylated in the presence as catalyst of either a cation-exchangeable layered clay or a cation-exchangeable stabilized pillared layered clay.

36 Claims, No Drawings

PROCESS FOR THE TRANSALKYLATION OR DEALKYLATION OF ALKYL AROMATIC HYDROCARBONS

The present invention relates in general to a process for the transalkylation or dealkylation of alkyl aromatic hydrocarbons and in particular to a process for the transalkylation or dealkylation of alkyl aromatic hydrocarbons using cation-exchangeable layered clays or cation-exchangeable stabilised pillared layered clays as catalysts.

Natural and synthetic clays having a lamellar structure with interlamellar spaces disposed between the lamellar layers are well known. Smectites, such as bentonite and montmorillonite are a class of clays possessing such a lamellar structure. Montmorillonite has an idealised stoichiometric composition corresponding to $Na_{0.67}[Al_{3.33}Mg_{0.67}](Si_8)O_{20}(OH)_4$. Structurally it comprises a central layer containing octrahedrally coordinated aluminium and magnesium in the form of their oxides and hydroxides sandwiched between two layers containing tetrahedrally coordinated silicon essentially in the form of its oxide. Normally in nature cations are present to compensate for the charge imbalance caused by isomorphous substitution of $Mg^{2+}$ for $Al^{3+}$ in the octahedral layer, and/or $Al^{3+}$ or other ions for $Si^{4+}$ in the tetrahedral layers. The octahedral and tetrahedral regions are tightly bound together to form a lamellar layer. The space between these lamellar layers, ie the interlamellar space, in natural clays is normally occupied by exchangeable $Ca^{2+}$ or $Na^+$ ions. The distance between the interlamellar layers can be increased substantially by absorption of various polar molecules such as water, ethylene glycol, amines etc, which enter the interlamellar space and in doing so push the layers apart. The interlamellar spaces tend to collapse when the molecules occupying the space are removed by, for example, heating the clays at high temperature.

Also known from U.S. Pat. Nos. 4,216,188 and 4,248,739 are stabilised pillared layered clays in which the layers are separated and supported by "pillars" of monomeric, oligomeric or polymeric species derived from metal hydroxides. Such clays can inherently possess a higher degree of thermal stability and improved hydrothermal stability when compared with non-pillared layered clays. In U.S. Pat. No. 4,248,739 the use of the pillared layered clays as sorbents, catalysts and catalytic supports is described. Similar uses are described for the pillared clays of U.S. Pat. No. 4,216,188.

Our European patent applications publication Nos. 0031252 and 0031687 disclose the use of cation-exchangeable layered clays in reactions capable of catalysis by protons, such as the production of alkyl aromatic compounds by reacting one or more aromatic compounds with one or more olefins or alcohols, eg the production of ethyl benzene by reacting benzene with ethylene, and isopropylbenzene by reacting benzene with propylene at elevated temperatures. Our European patent application publication No. 0083970 of earlier priority date describes the use of stabilised pillared interlayered clays in reactions capable of being catalysed by protons, such as the production of alkyl aromatic compounds by reacting one or more aromatic compounds with one or more olefins or alcohols, eg the production of ethyl benzene by reacting benzene with ethylene and isopropylbenzenes by reacting benzene with propylene at elevated temperature. Furthermore, U.S. Pat. No. 2,945,072 describes and claims a process for producing propylated benzenes of lower molecular weight by reacting an aromatic compound of the group consisting of benzene and halo-substituted benzenes with polypropylated benzenes in the liquid phase in the presence of an acid-activated, non-swellable, bentonite-type clay having a base exchange capacity of at least about 20 and at a temperature of about 90° to 130° C. Clays suitable for use in the process of U.S. Pat. No. 2,945,072 include acid-activated montmorillonite-type clays, as well as acid-activated Fuller's earth having the minimum base exchange capacity. For the purpose of the invention of U.S. Pat. No. 2,945,072, a non acid-activated clay may be activated by boiling for about one hour a slurry of 1 part by weight of clay to 10 parts by weight of 5% sulphuric acid, followed by separation of the acid from the clay, first by settling and decantation and then by wringing the wet clay. Such treatment, in our experience, wholly or partly destroys the layered structure of the clay and produces a clay containing residual mineral acid. Cation-exchanged layered clays and stabilised pillared interlayered clays are distinguished from acid-activated clays in the principal respects that their layered structure is essentially intact and they contain substantially no residual acid.

We have now found that cation-exchangeable layered clays, as described in European patent publications Nos. 0031252 and 0031687, and cation-exchangeable pillared clays as described in UK application No. 8200633 are active as catalysts for the transalkylation or dealkylation of alkyl aromatic hydrocarbons.

The term "transalkylation" as conventionally employed and as used in the context of this specification means the exchange of alkyl substituent groups between aromatic hydrocarbons. The aromatic hydrocarbons can comprise a single alkyl substituted aromatic hydrocarbon or a mixture of aromatic hydrocarbons, provided that in the case of a mixture at least one of the components is an alkyl substituted aromatic hydrocarbon. Examples of transalkylation reactions include:

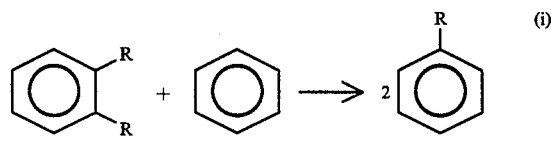

and,

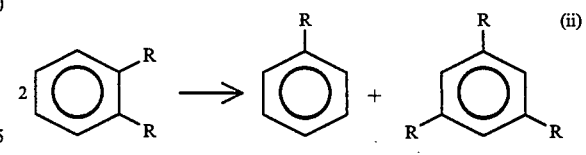

which is also commonly called disproportionation, and

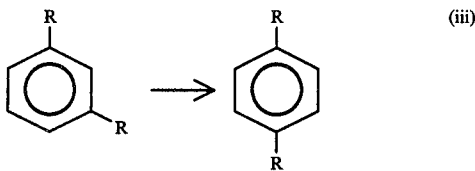

which is also commonly called isomerisation.

The term "dealkylation" as conventionally employed and as used in the context of this specification means the removal of an alkyl group or groups from an alkyl substituted aromatic hydrocarbon without reference to the ultimate fate of the alkyl group moiety. An example of dealkylation is:

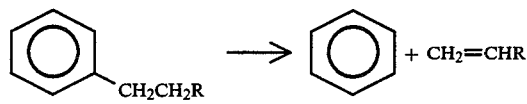

Catalysts known to be active for the alkylation of aromatic hydrocarbons may be very much less active catalysts for transalkylation. Thus, for example, the supported phosphoric acid catalyst commonly employed for the production of cumene from benzene and propylene at about 230° C. and about 30 bar pressure is almost inactive for transalkylation of the co-produced di-isopropyl benzenes with benzene under these conditions.

Also in the context of this specification, the term "cation" is used in its broadest sense to include "protons or hydrogen ions" as cations.

Accordingly, the present invention provides a process for the catalysed transalkylation or dealkylation of alkyl aromatic hydrocarbons wherein the alkyl group is a $C_1$ to $C_{10}$ alkyl group under transalkylation or dealkylation conditions *characterised in that* the catalyst is either a cation-exchangeable layered clay or a cation-exchangeable stabilised pillared layered clay.

The layered clay may suitably be either a natural clay or a synthetic clay. Suitably the clay may be a smectite-type clay, which may be of the dioctahedral type or the trioctahedral type, preferably the dioctahedral type, for example bentonite, montmorillonite, beidellite or nontronite. Reference is made to the book entitled "The Chemistry of Clay-Organic Reactions" by B. K. G. Theng published by John Wiley and Sons, New York-Toronto, at page 2 for an explanation of the difference between dioctahedral- and trioctahedral-type layered clays.

As hereinbefore mentioned, the clays in their natural state normally contain exchangeable cations, such as sodium or calcium ions, in the interlamellar space. Such clays have some catalytic activity in the process of the present invention. In order to bestow increased catalytic activity on the natural clay it is necessary to exchange some or all of the exchangeable metal cations with one or more other suitable cations. In the case of synthetic clays suitable cations may be present in the clays as synthesised, thereby eliminating any need for cation-exchange, or may be introduced thereafter as with the natural clays.

The cations normally associated with layered clays may suitably be exchanged with either hydrogen ions or cations of the metals chromium, aluminium, cobalt, nickel, iron, copper or vanadium. Preferably the layered clays are exchanged with either hydrogen ions, chromium ions or aluminium ions.

Cation-exchange of layered clays may be effected by any technique which essentially preserves the layered structure of the clay. A general discussion of the factors affecting cation-exchange may be found in the aforesaid European patent applications publication Nos. 0031252 and 0031687 to which the reader is referred for further details. With regard to the smectite-type hydrogen ion-exchanged clay for example, hydrogen ion-exchange is preferably effected by contacting the clay containing exchangeable cations with a solution containing appropriate cations under ion-exchange conditions. Preferably the solution of the acid is an aqueous solution. Suitable acids are mineral acids, including sulphuric and hydrochloric acid, but other acids, such as carboxylic acids may be used if so desired. The acid may suitably be from 0.5 to 10 molar. Although contact of the clay with the mineral acid is preferably effected at or near ambient temperature, elevated temperatures which do not destroy the layered structure and the catalytic activity of the clay may be employed, eg up to about 35° C. The period of contact will depend to some extent on the temperature. Typically, at ambient temperature the contact period may be in the range from ½ hour to 3 days.

Techniques for separating the cation-exchanged layered clay from the ion-exchange media and excess ions are well known. Any suitable solid/liquid separation procedure can be used. Decantation and centrifugation are two preferred methods for solid/liquid separation.

After exchange, the cation-exchanged layered clays are preferably washed until all extraneous metal cations are removed. Thereafter the clay is preferably dried. Although drying is preferably effected at elevated temperature, temperatures which cause collapse of the layered structure should be avoided. Generally, for cation-exchanged smectites drying temperatures in the range 20° to 120° C. are suitable. The clays may suitably be activated before use as catalysts by heating in air at a temperature which does not collapse the layered structure, suitably up to 180° C., preferably from 80° to 150° C. for hydrogen ion-exchanged smectites; suitably up to about 200° C., preferably from 80° to 200° C. for metal cation-exchanged clays. The catalyst may suitably be combined with other compounds, for example silica, in order to aid pellet or particle stability.

Suitable stabilised pillared layered clays which may be used in the invention and methods for making them include those described and claimed in the specifications of U.S. Pat. Nos. 4,216,188 and 4,248,739. Typically, the pillared clay may be prepared by reacting a colloidal solution of a mono-ionic montmorillonite having a concentration of 100 mg to 800 mg montmorillonite per liter, in the form of fully dispersed negatively charged unit layers at room temperature with an aged sol of a metal hydroxide aged for at least 5 days at ambient temperature, said metal hydroxide being selected from the group consisting of aluminium hydroxide and chromium hydroxide, at a pH adjusted below the zero charge point having a residual net positive charge on the said metal hydroxide, under vigorous agitation, resulting in a rapid flocculation of the montmorillonite cross-linked with said metal hydroxide, separating the product from the liquid phase, and stabilising the product by heat treatment. Further details of this process may be found in U.S. Pat. No. 4,216,188. Alternatively, the pillared clay may suitably be prepared by reacting a smectite-type clay, such as bentonite, with an aqueous solution of a polymeric cationic hydroxy inorganic metal complex, such as chlorhydrol. Further details of this method may be found in U.S. Pat. No. 4,248,739.

The pillared clays may suitably be modified by cation-exchange following treatment with a base, for example ammonia. The nature of this process is described in U.S. Pat. No. 4,248,739 for example, to which the reader is referred for further details.

Alternatively, the catalyst may be a stabilised pillared layered clay in which the pillars are formed after exchanging the natural cations of the clay with more suitable cations, as hereinbefore described. The preparation of stabilised pillared layered clays according to this procedure is described in, for example, U.S. Pat. No. 4,238,364.

With regard to the dealkylation and transalkylation reactions, the alkyl aromatic hydrocarbon may suitably be a mono- or poly-$C_1$ to $C_{10}$-alkyl substituted benzene, naphthalene or other polycyclic aromatic hydrocarbon. The alkyl substituent may, if desired, be functionalised, that is it may be, for example, an alkoxy or hydroxyalkyl substituent. Alternatively, in addition to alkyl substituent(s) the aromatic hydrocarbon may contain other substituents, such as for example hydroxyl groups. Preferably the alkyl aromatic compound is an alkyl benzene. Mixtures of alkyl aromatic hydrocarbons may also be employed. Furthermore, inert diluents such as for example aliphatic hydrocarbons or naphthenes may be employed if so desired. Suitable mixtures include those containing alkyl aromatic hydrocarbons obtained by the distillation or fractionation of petroleum refinery streams, such as those derived from catalytic or steam crackers.

It will be appreciated by those skilled in the art that one or more types of transalkylation reactions as hereinbefore defined may occur in certain reaction mixtures, the scope for and extent of these different types of transalkylation reactions being dependent on, amongst other factors, the nature of the reactants.

A preferred transalkylation reaction is the reaction of a dialkyl benzene, wherein the alkyl substituent is ethyl or isopropyl, with benzene to produce the corresponding monoalkyl benzene, eg the reaction of diisopropylbenzene with benzene to produce isopropylbenzene (cumene). Mixtures of dialkyl benzenes with other alkyl benzenes, eg trialkyl benzenes, may be employed.

Another preferred transalkylation reaction is the conversion of toluene to a product comprising benzene and xylenes.

Another preferred transalkylation reaction is the conversion of diisopropylbenzene into a product comprising monoisopropyl benzene and triisopropylbenzene.

Another preferred transalkylation reaction is the isomerisation of polyalkylbenzenes, for example the isomerisation of meta-diisopropylbenzene to a product predominantly comprising meta- and para-diisopropylbenzenes.

Transalkylation may be effected in the liquid phase or in the vapour phase. The conditions under which transalkylation may be effected will depend to some extent on the reactants selected and on whether the process is operated in the liquid phase or the vapour phase. Generally in the liquid phase elevated temperatures, suitably in the range 100° to 450° C., preferably from 150° to 300° C., may be employed, and the pressure may suitably be at least the pressure required to maintain the reactants in the liquid phase at the reaction temperature. Generally in the vapour phase, elevated temperatures, suitably in the range 100° to 450° C. may be employed.

The particular clay catalyst employed will also depend on the conditions selected. Normally, the cation-exchangeable layered clays are preferred in both the liquid and vapour phases at lower operating temperatures within the aforesaid ranges, but at the higher temperatures the cation-exchangeable stabilised pillared layered clays are preferred.

The transalkylation and/or dealkylation reactions may conveniently be carried out concurrently with alkylation.

Accordingly, in a preferred embodiment (A) the invention comprises reacting in the liquid phase in an alkylation zone an aromatic hydrocarbon with an alkylating agent selected from $C_2$ to $C_{10}$ alcohols and olefins, and optionally also an inert diluent, under alkylation conditions in the presence as catalyst of a cation-exchangeable layered clay or stabilised pillared layered clay as hereinbefore described to form a product comprising unreacted aromatic hydrocarbon, monoalkylated aromatic hydrocarbon and polyalkylated aromatic hydrocarbon, recovering some or all of the monoalkylated aromatic hydrocarbon and some or all of the inert diluent if present from the product and either:
(a) recycling all or part of the remainder of the product comprising aromatic hydrocarbon, inert diluent if any, any monoalkylated aromatic hydrocarbon and polyalkylated aromatic hydrocarbon with the feed to the alkylation zone, or
(b) passing all or part of the remainder of the product comprising aromatic hydrocarbon, inert diluent if any, any monoalkylated aromatic hydrocarbon and polyalkylated aromatic hydrocarbon, optionally with additional aromatic hydrocarbon and/or polyalkylated aromatic hydrocarbon, to a transalkylation and/or dealkylation zone wherein it is contacted with a catalyst comprising a cation-exchangeable layered clay or stabilised pillared layered clay as hereinbefore described under transalkylation and/or dealkylation conditions and recovering therefrom a monoalkylated aromatic hydrocarbon, or (c) separating the aromatic hydrocarbon and some or all of the inert diluent if present from the polyalkylated aromatic hydrocarbon, passing the polyalkylated aromatic hydrocarbon and any remaining inert diluent to a transalkylation and/or dealkylation zone wherein it is contacted with a cation-exchangeable layered clay or stabilised pillared layered clay catalyst as hereinbefore described under transalkylation and/or dealkylation conditions and recovering a monoalkylated aromatic hydrocarbon therefrom.

In certain circumstances it may be preferable to carry out the alkylation reaction and the transalkylation and/or dealkylation reactions separately. By operating in this manner the formation of undesirable by-products can be reduced.

Accordingly in a further preferred embodiment (B) the invention comprises in a first step reacting in the liquid phase in an alkylation zone under alkylation conditions an aromatic hydrocarbon with an alkylating agent selected from $C_2$ to $C_{10}$ alcohols and olefins, optionally in the presence of an inert diluent, in the presence of a cation-exchangeable layered clay or stabilised pillared layered clay to form an alkylation product comprising unreacted aromatic hydrocarbon, monoalkylated aromatic hydrocarbon, polyalkylated aromatic hydrocarbon and inert diluent if present and in a separate second step reacting the alkylation product from the first step in a transalkylation and/or dealkylation zone under transalkylation and/or dealkylation conditions in the presence of a catalyst comprising a cation-exchangeable layered clay or stabilised pillard layered clay so as to increase the proportion of the monoalkylated aromatic hydrocarbon in the alkylation product, recovering some or all of the monoalkylated aromatic hydrocarbon and some or all of the inert diluent if present and thereafter recycling all or part of the remainder of the product comprising aromatic hydrocarbon, any monoalkylated aromatic hydrocarbon, polyalkylated aromatic hydrocarbon and any inert diluent either:
(a) with the feed to the transalkylation and/or dealkylation zone, or
(b) with the feed to the alkylation zone, or
(c) both (a) and (b).

In the preferred embodiments (A) and (B) the aromatic hydrocarbon may suitably be benzene or naphthalene, preferably benzene. The olefin may suitably be ethylene, propylene or a butene, preferably propylene. Suitable alcohols are ethanol, n-propanol and isopropanol. Preferably the alkylating agent is an olefin. Preferably the aromatic hydrocarbon is benzene, the alkylating agent is ethylene or propylene and the monoalkylated aromatic hydrocarbon is ethyl benzene or isopropylbenzene. The inert diluent may be a substantially pure hydrocarbon or mixtures of hydrocarbons, preferably those contained in refinery streams obtained by distillation or fractionation and/or hydrogenation and which contain substantial amounts of the desired olefin or aromatic hydrocarbon.

Alkylation conditions may suitably be a temperature up to 400° C., preferably in the range 100° to 300° C., and an elevated pressure at least sufficient to maintain a liquid phase. In the preferred embodiment (B) the alkylation conditions are preferably such that substantial transalkylation and/or dealkylation is avoided in the alkylation zone and the transalkylation and/or dealkylation conditions are preferably such that transalkylation and/or dealkylation is favoured in the transalkylation and/or dealkylation zone. Suitably this may be achieved by operating the alkylation zone and the transalkylation and/or dealkylation zone at different temperatures, the values of which will depend on the nature of the reactants and the reaction times or flow rates of the reactants. In the case of the production of cumene from propylene and benzene, for example, using a residence time of about 30 minutes and a hydrogen ion-exchanged layered clay, the alkylation zone may suitably be maintained at a temperature in the range from 125° to 150° C. and the transalkylation zone may suitably be maintained at a higher temperature, preferably in the range from about 150° to 170° C.

The steps of recovery and separation may suitably be accomplished by fractional distillation.

The process of the invention may suitably be carried out batchwise or continuously, preferably continuously.

The invention will now be further illustrated by reference to the following Examples.

PREPARATION OF CATION-EXCHANGED LAYERED CLAYS AND STABILISED PILLARED LAYERED CLAYS

Hydrogen Ion-Exchanged Wyoming Bentonite (A)

Sodium bentonite (a Wyoming Bentonite supplied as a fine powder for use in drilling muds) was added to a solution of concentrated sulphuric acid (400 ml) in water (100 ml) and left at room temperature for 2 days with occasional stirring. The clay was separated from the solution and washed with water by repeated centrifuging and resuspending in water until the pH of the supernatant solution was the same as the distilled water used in the washing. The clay was dried at 80° C. in air and ground to give a fine powder (for batch reactions) or granules (for continuous reactions) of hydrogen bentonite.

Aluminium Ion-Exchanged Wyoming Bentonite (B)

Wyoming bentonite powder (100 g) was added to a solution of aluminium sulphate $[Al_2(SO_4)_3.16H_2O]$ (250 g) in distilled water (1.5 liter) and left overnight. The clay was centrifuged, mixed with a further 1.5 liters of water and recentrifuged. This was repeated a second time to remove all extraneous ions. Finally, the aluminium ion-exchanged clay was oven dried at 80° C.

Alumina Pillared Wyoming Bentonite (C)

Wyoming bentonite (600 g) was added into the vortex of a well stirred solution of chlorhydrol (600 g of 50% aqueous solution) in 12 liters of deionised water. The pH of the solution was adjusted to 5.5 by adding dilute ammonia solution. The vigorously stirred solution was then heated at 65° C. for one hour whilst the pH was maintained at 5.5 by further additions of ammonia solution. On cooling to room temperature, the clay was centrifuged, added to a further 12 liters of deionised water, stirred and recentifuged, and washed until free of all extraneous ions. The alumina pillared Wyoming bentonite was made by drying the clay at 80° C., then heat treating at 400° C. for 4 hours. The alumina pillared Wyoming bentonite showed a strong $d_{001}$ absorption band at 17.9 Å in its X-ray diffraction spectrum.

Hydrogen Ion-Exchanged Alumina Pillared Wyoming Bentonite (D)

The alumina pillared Wyoming bentonite (C), previously heat treated at 400° C. for 4 hours in air was ground to granules of 1–2 mm, immersed in a 1M solution of potassium hydroxide solution and left overnight. The granules were filtered on a sintered glass funnel and washed with water until all extraneous ions were removed. The granules were then immersed in a dilute sulphuric acid solution, prepared by mixing 100 ml of concentrated sulphuric acid and 500 ml deionised water, and left overnight. The granules were filtered on a sintered glass funnel, washed with water until free of all extraneous ions, and dried at 80° C. in air. The granules of hydrogen ion-exchanged alumina pillared Wyoming bentonite so prepared had a very strong X-ray diffraction absorption at 16.0 Å corresponding to the $d_{001}$ spacing.

Aluminium Ion-Exchanged Alumina Pillared Wyoming Bentonite (E)

A similar preparation to that for hydrogen ion-exchanged alumina pillared Wyoming bentonite (C), except that the dilute sulphuric acid solution was replaced by a 1M solution of aluminium chloride, was carried out. The granules of aluminium ion-exchanged alumina pillared Wyoming bentonite showed a strong X-ray diffraction $d_{001}$ absorption at 17.2 Å.

EXAMPLE 1

Benzene (60 g, 0.77 mole), diisopropylbenzene (12.5 g, 0.077 mole consisting of the ortho-, meta-, and para-isomers in the proportion of 1:2.8:0) and hydrogen ion-exchanged Wyoming bentonite (A) (5 g) were added to a 150 ml stainless steel autoclave fitted with a magnetic stirrer. The autoclave was sealed, charged to 20 bar with nitrogen and stirred (400 rpm) at 230° C. for 2.5 hours when a maximum pressure of 45 bar was obtained. On cooling, gaseous products were vented off, and the catalyst and liquid products removed. The liquid products (68.0 g) contained benzene (52.6 g), cumene (11.1 g) and diisopropylbenzene (2.6 g) as major products. The diisopropylbenzene product consisted of the ortho-, meta- and para-isomers in the proportion of trace: 3.0:1. Cumene was made in a 120% molar yield from reactant diisopropylbenzene at a selectivity of 76%, assuming two molecules of cumene are produced from the reaction of one molecule of diisopropylbenzene.

Comparison Test 1

Example 1 was repeated but using 5 g of a commercially available supported phosphoric acid alkylation catalyst supplied by UOP for the production of cumene from benzene and propylene at about 230° C. instead of the hydrogen ion-exchanged Wyoming bentonite (A) catalyst. The liquid products (66.7 g) contained benzene (56.0 g), cumene (0.2 g) and diisopropylbenzene (10.3 g) as major components. The diisopropylbenzene product consisted of the ortho-, meta- and para-isomers in the proportion of 1:2.8:0. The total recovery of liquid products was 92% w/w, the recovery of unchanged diisopropylbenzene was 82.4% w/w and the yield of cumene was 20.6% molar based on reactant diisopropyl benzene.

This example illustrates the low activity of this effective alkylation catalyst for transalkylation reactions.

EXAMPLE 2

A mixture of benzene and diethylbenzene (ortho-, meta-, para-isomer ratio of 1:3.7:1.2) in the molar proportions of 68:32 respectively was fed over alumina-pillared Wyoming bentonite (C) contained in a glass tube at 390° C. The vapour had a residence time (catalyst volume/volume of vapour flow per second) of 12 seconds. An examination of the liquid products produced between 20 and 25 minutes on stream showed benzene (68% molar), ethylbenzene (19%) and diethylbenzene (10%) as major products. The diethylbenzene was present in an ortho-, meta-, para-isomer ratio of 1:6:3.

After a period of time, catalyst activity was reduced. Complete catalytic activity was recovered by passing air over the catalyst maintained in the region of around 400° C.

EXAMPLE 3

Benzene (120 g, 1.54 mole), diethylbenzene (12 g, 0.090 mole, consisting of the ortho-, meta-, and para-isomers in the proportion of 1:16:5) and the hydrogen ion-exchanged Wyoming bentonite (A) (5 g) were sealed in a 150 ml stainless steel autoclave fitted with a magnetic stirrer, and stirred (600 rpm) at 200° C. for 2.5 hours when a maximum pressure of 20 bar was obtained. On cooling, the gaseous products were vented off, and the catalyst and liquid products removed. The liquid products contained benzene (119.5 g), ethylbenzene (3.8 g), diethylbenzene (6.7 g) and triethylbenzene (1.8 g) as major products. The diethylbenzene product consisted of the ortho-, meta-, para-isomers in the proportion of 1:11.6:4.5, and represented 57% of the reactant diethylbenzene showing transalkylation of diethylbenzene.

EXAMPLE 4

Benzene (120 g, 1.54 mole), diisopropylbenzene (16.0 g, 0.099 mole consisting of the ortho-, meta-, and para-isomers in the proportion of 1:2.8:0) and hydrogen ion-exchanged Wyoming bentonite (A) (5 g) were added to a 150 ml stainless steel autoclave fitted with a magnetic stirrer. The autoclave was sealed and charged with liquid propylene (25 ml, 13.0 g, 0.309 mole) and stirred at 230° C. for 2.5 hours when a maximum pressure of 26 bar was obtained. On cooling, gaseous products were vented off, and the catalyst and liquid products removed. The results are shown in the Table.

EXAMPLE 5

Example 4 was repeated but with 12 g instead of 16 g of diisopropylbenzene. The results are shown in the Table.

EXAMPLE 6

Example 4 was repeated but with 8 g instead of 16 g of diisopropylenebenzene. The results are shown in the Table.

EXAMPLE 7

Example 4 was repeated but with 4 g instead of 16 g of diisopropylbenzene. The results are shown in the Table.

EXAMPLE 8

Example 4 was repeated but with 2 g instead of 16 g of diisopropylbenzene. The results are shown in the Table.

EXAMPLE 9

Example 4 was repeated but with 6 g of meta-diisopropylbenzene instead of 16 g of the mixed isomer diisopropylbenzene. The results are shown in the Table.

EXAMPLE 10

Example 4 was repeated but with 12 g of meta-diisopropylbenzene instead of 12 g of the mixed isomer diisopropylbenzene. The results are shown in the Table.

EXAMPLE 11

Example 4 was repeated but with 12 g of para-diisopropylbenzene instead of 12 g of the mixed isomer diisopropylbenzene. The results are shown in the Table.

EXAMPLE 12

Example 5 was repeated except that the hydrogen ion-exchanged Wyoming bentonite (A) was replaced by the aluminium ion-exchanged Wyoming bentonite (B). The results are shown in the Table.

Comparison Test 2

Example 9 was repeated but using 5 g of a commercially available supported phosphoric acid alkylation catalyst supplied by UOP for the production of cumene from benzene and propylene at about 230° C. instead of the hydrogen ion-exchanged Wyoming bentonite (A). The liquid products (132.6 g) contained cumene (28.6 g) and diisopropylbenzene (6.3 g) compared to cumene (42.1 g) and diisopropylbenzene (3.5 g) in Example 9. This result illustrates the lower activity of this excellant alkylation catalyst for transalkylation reactions.

EXAMPLE 13

A feedstock consisting of benzene (90.9% by weight), propylene (3.4% by weight) and meta-diisopropylbenzene (5.7% by weight) was passed over hydrogen ion-exchanged Wyoming bentonite particles (A) (mesh size 2 to 3 mm) maintained at 230° C. and 30 bar. The residence time (catalyst volume/volume of liquid flow per minute) was maintained at 50 minutes. Analysis of a typical sample of liquid product showed benzene (81.8% by weight), cumene (15.9% by weight), diisopropylbenzene (2.1% by weight, o:m:p isomer ratio of 0:3.6:1) as major products. Over 63% of the diisopropylbenzene in the feed is converted mainly into cumene.

EXAMPLE 14

A feedstock consisting of benzene (87.4% by weight), propylene (7.6% by weight) and meta-diisopropylbenzene (5.0% by weight) was passed over particles (mesh size 2 to 3 mm) of the hydrogen ion-exchanged Wyoming bentonite (A) maintained at 178° C. and 30 bar. The residence time was maintained at 35 minutes. Analysis of a typical sample of liquid product showed benzene (71% by weight), cumene (24.5% by weight) and diisopropylbenzene (3.5% by weight, o:m:p isomer ratio of trace:2.5:1) as major products. Over 30% of the diisopropylbenzene in the feed was converted, mainly into cumene.

EXAMPLE 15

Example 14 was repeated but the hydrogen ion-exchanged Wyoming bentonite (A) was replaced with the hydrogen ion-exchanged alumina pillared Wyoming bentonite (C). Analysis of a typical sample of liquid product showed benzene (69% by weight), cumene (25% by weight), and diisopropylbenzene (3.5% by weight, o:m:p isomer ratio of trace:2.7:1). Over 35% of the diisopropylbenzene in the feed was converted, mainly into cumene.

EXAMPLE 16

Example 14 was repeated but the hydrogen ion-exchanged Wyoming bentonite (A) was replaced with the aluminium ion-exchanged alumina pillared Wyoming bentonite (E). Analysis of a typical sample of liquid product showed benzene (74% by weight), cumene (22% by weight) and diisopropylbenzene (4% by weight, o:m:p isomer ratio of trace:2.1:1). Over 20% of the diisopropylbenzene in the feed was converted, mainly into cumene.

EXAMPLE 17

Example 4 was repeated but using benzene (70 g, 0.90 mole), hexane (50 g, 0.60 mole), propylene (10.3 g 0.25 mole) and hydrogen ion-exchanged Wyoming bentonite (A) (5 g) at a reaction temperature of 230° C. The liquid products (130 g) contained benzene (36.8% w/w), cumene (23.2%), and diisopropylbenzene (4.4%) together with hexane as major products. The diisopropylbenzene was present in an ortho-, meta-, para-isomer ratio of 0:2.1:1 which is the proportion expected from alkylation and transalkylation reactions.

EXAMPLE 18

Diisopropylbenzene (with the ortho-, meta-, para-isomer ratio of 2.1:1.1:1.0) was heated (ca. 205° C.) over hydrogen ion-exchanged Wyoming bentonite (A) (weight ratio of diisopropylbenzene to catalyst=3.3:1) in a glass flask fitted with a condenser. After 20 minutes at ca. 205° C., the liquid reaction mixture contained 60% w/w diisopropylbenzene, 23% triisopropylbenzene and 16% cumene as major products. After 70 minutes at ca. 205° C. the reaction mixture contained 53% w/w diisopropylbenzene, 24% cumene and 22% triisopropylbenzene. Both samples contained diisopropylbenzene in an ortho-, meta-, para-isomer ratio of 0:2.0:1.

EXAMPLE 19

Para-diisopropylbenzene was heated as in Example 18 but with a para-diisopropylbenzene to hydrogen ion-exchanged Wyoming bentonite ratio of 7:1. After 80 minutes at 205° C., the liquid reaction mixture contained diisopropylbenzene (51% w/w), triisopropylbenzene (25%) and cumene (15%) as major products. The diisopropylbenzene had an ortho-, meta-, para-isomer ratio of 0:2:1.

EXAMPLE 20

A mixture of benzene (120 g, 1.54 mole) and meta-xylene (12 g, 0.11 mole) were heated over hydrogen ion-exchanged Wyoming bentonite (A) in the autoclave used in the previous experiments at 200° C. for 2.5 hours under autogeneous pressure. The liquid product contained xylenes in the ortho- plus meta- to para-isomer ratio of 5:1. Complete analytical separataion of the ortho- and meta-xylene isomers was not achieved, but the appearance of para-xylene shows that isomerisation is occurring over the hydrogen ion-exchanged Wyoming bentonite.

EXAMPLE 21

Ethyl tertiary-butyl benzene (5 g) and hydrogen ion-exchanged Wyoming bentonite (A) (1 g) were heated in a glass flask under gentle reflux. Isobutene was evolved and after one hour the liquid reaction products contained 11% by weight of ethyl benzene.

This Example illustrates the dealkylation of ethyl tertiary-butyl benzene.

EXAMPLE 22

(Two-Stage Reaction)

In a first stage a feedstock consisting of benzene (85.4% w/w) and propylene (14.6% w/w) was passed over hydrogen ion-exchanged Wyoming bentonite particles (mesh size 2 to 5 mm) maintained at 140° C. and 30 bar. The residence time (catalyst volume/volume of liquid flow per minute) was maintained at 35 minutes. Analysis of a typical sample of liquid product showed benzene (62.8% w/w), cumene (29.6% w/w), diisopropylbenzenes (6.55% w/w) and triisopropylbenzene (0.62% w/w) as major components. The ratio of diisopropylbenzene isomers was ortho:meta:para about 1:29:13.6 and that of 1,3,5- to 1,2,4-triisopropylbenzenes was 6.8:1.

In a second stage this product was then passed over an identical catalyst bed maintained at 165° C. and 30 bar. The residence time was maintained at 45 minutes. Analysis of a typical sample of liquid product showed benzene (61.8% w/w), cumene (32.9% w/w), diisopropyl benzenes (4.6% w/w) and triisopropylbenzenes (0.1% w/w) as major components. The ratio of diisopropylbenzene isomers was ortho:meta:para about trace:2.3:1.0, and 1,2,5-triisopropylbenzene was the only triisopropylbenzene isomer observed.

This example illustrates a two stage process in which the first stage consists of an essentially alkylation process and the second stage a transalkylation process.

TABLE

Simultaneous alkylation and transalkylation
Benzene + propylene + diisopropylbenzene

| Example No | Total Weight of Reactants (g) | Weight of Liquid Products Recovered (g) | Weight of Diisoproylbenzenes In Reactants (g) | Weight of Diisoproylbenzenes In Products (g) | Ratio of Diisopropylbenzenes In Reactants o:m:p | Ratio of Diisopropylbenzenes In Products o:m:p | Weight of Cumene Produced (g) |
|---|---|---|---|---|---|---|---|
| 4 | 149 | 143.3 | 16 | 11.3 | 1:2.8:0 | 0:2.1:1 | 46.3 |
| 5 | 145 | 139.3 | 12 | 6.9 | 1:2.8:0 | 0:2.5:1 | 38.3 |
| 6 | 141 | 134.0 | 8 | 4.9 | 1:2.8:0 | 0:2.3:1 | 39.4 |
| 7 | 137 | 130.6 | 4 | 4.7 | 1:2.8:0 | 0:2.3:1 | 38.5 |
| 8 | 135 | 125.5 | 2 | 3.0 | 1:2.8:0 | 0:2.3:1 | 29.2 |
| 9 | 139 | 132.8 | 6 | 3.5 | 0:1:0 | 0:2.3:1 | 42.1 |
| 10 | 145 | 141.8 | 12 | 7.0 | 0:1:0 | 0:2.3:1 | 55.2 |
| 11 | 145 | 139.8 | 12 | 6.9 | 0:0:1 | 0:2.3:1 | 48.8 |
| 12 | 145 | 141.7 | 12 | 3.8 | 0:1:0 | 0:2.3:1 | 38.8 |

We claim:

1. A process for the catalysed transalkylation of alkyl aromatic hydrocarbons wherein the alkyl group is a $C_1$ to $C_{10}$ alkyl group under transalkylation conditions characterised in that the catalyst is either a cation-exchangeable layered clay or a cation-exchangeable stabilised pillared layered clay.

2. A process according to claim 1 wherein the layered clay or the stabilised pillared layered clay is exchanged with either hydrogen ions or cations of the metals chromium, aluminium, cobalt, nickel, iron, copper or vanadium.

3. A process according to claim 1 wherein the catalyst is a layered clay of the dioctahedral smectite-type.

4. A process according to claim 1 wherein the catalyst is a stabilised pillared layered clay.

5. A process according to claim 1 wherein the catalyst is the stabilised pillared layered clay obtained by reacting a smectite-type clay with an aqueous solution of a polymeric cationic hydroxy inorganic metal complex.

6. A process according to claim 1 wherein the transalkylation reaction is the reaction of a dialkylbenzene, wherein the alkyl substituent is ethyl or isopropyl, with benzene to produce the corresponding monoalkylbenzene.

7. A process according to claim 1 wherein the transalkylation reaction is the conversion of toluene to a product comprising benzene and xylenes.

8. A process according to claim 1 wherein the transalkylation reaction is the conversion of diisopropylbenzene into a product comprising monoisopropylbenzene and triisopropylbenzene.

9. A process according to claim 1 wherein the transalkylation reaction is the conversion of meta-diisopropylbenzene to a product predominantly comprising meta- and para-diisopropylbenzenes.

10. A process according to claim 1, further characterised in that the temperature is in the range of 100° C. to 450° C.

11. A process according to claim 1, further characterised in that the temperature is in the range of 150° C. to 300° C.

12. A process for the catalysed transalkylation of an alkyl aromatic hydrocarbon comprising reacting in the liquid phase in an alkylation zone an aromatic hydrocarbon with an alkylating agent selected from $C_2$ to $C_{10}$ alcohols and olefins under alkylation conditions in the presence as catalyst of a cation-exchangeable layered clay or stabilised pillared layered clay to form a product comprising unreacted aromatic hydrocarbon, monoalkylated aromatic hydrocarbon and polyalkylated aromatic hydrocarbon, recovering at least some of the monoalkylated aromatic hydrocarbon from the product.

13. A process according to claim 12, wherein the identical catalyst is utilized in the alkylation zone, and in the transalkylation zone.

14. A process according to claim 12, further comprising
recycling at least part of the remainder of the product comprising aromatic hydrocarbon, any monoalkylated aromatic hydrocarbon and polyalkylated aromatic hydrocarbon with the feed to the alkylation zone.

15. A process according to claim 12, further comprising
passing at least part of the remainder of the product comprising aromatic hydrocarbon, any monoalkylated aromatic hydrocarbon and polyalkylated aromatic hydrocarbon, to a transalkylation zone wherein it is contacted with a catalyst comprising a cation-exchangeable layered clay or stabilised pillared interlayered clay under transalkylation conditions and recovering therefrom a monoalkylated aromatic hydrocarbon.

16. A process according to claim 12, further comprising
separating the aromatic hydrocarbon from the polyalkylated aromatic hydrocarbon, passing the polyalkylated aromatic hydrocarbon to a transalkylation zone wherein it is contacted with a cation-exchangeable layered clay or stabilised pillared layered clay catalyst under transalkylation conditions and recovering a monoalkylated aromatic hydrocarbon therefrom.

17. A process for the catalysed transalkylation of an alkyl aromatic hydrocarbon comprising reacting in a first step in the liquid phase in an alkylation zone under alkylation conditions an aromatic hydrocarbon with an alkylating agent selected from $C_2$ to $C_{10}$ alcohols and olefins, in the presence of a catalyst comprising a cation-exchangeable layered clay or stabilised pillared layered clay to form an alkylation product comprising unreacted aromatic hydrocaron, monoalkylated aromatic hydrocarbon, and polyalkylated aromatic hydrocarbon and in a separate second step reacting the alkylation product from the first step in a transalkylation zone under transalkylation conditions in the presence of a catalyst comprising a cation-exchangeable layered clay or stabilised pillared layered clay so as to increase the proportion of the monoalkylated aromatic hydrocarbon in the alkylation product, recovering at least some of the monoalkylated aromatic hydrocarbon and thereafter recycling at least part of the remainder of the product comprising aromatic hydrocarbon, any monoalkylated aromatic hydrocarbon, and polyalkylated aromatic hydrocarbon.

18. A process according to claim 17 wherein the alkylation conditions are such that substantial transalkylation is avoided in the alkylation zone and the transalkylation conditions are such that transalkylation is favoured in the transalkylation zone.

19. A process according to claim 17, wherein the identical catalyst is utilized in the alkylation zone, and in the transalkylation zone.

20. A process according to claim 17, wherein the recycling of at least part of the remainder of the product is with the feed to the transalkylation zone.

21. A process according to claim 17, wherein the recycling of at least part of the remainder of the product is with the feed to the alkylation zone.

22. A process according to claim 17, wherein the recycling of at least part of the remainder of the product is
 (a) with the feed to the transalkylation zone, and is
 (b) with the feed to the alkylation zone.

23. A process for the catalysed dealkylation of alkyl aromatic hydrocarbons wherein the alkyl group is a $C_1$ to $C_{10}$ alkyl group under dealkylation conditions characterised in that the catalyst is either a cation-exchangeable layered clay or a cation-exchangeable stabilised pillared layered clay.

24. A process according to claim 23 wherein the layered clay or the stabilised pillared layered clay is exchanged with either hydrogen ions or cations of the metals chromium, aluminium, cobalt, nickel, iron, copper or vanadium.

25. A process according to claim 23 wherein the catalyst is a layered clay of the dioctahedral smectite-type.

26. A process according to claim 23 wherein the catalyst is a stabilised pillared layered clay.

27. A process according to claim 23 wherein the catalyst is the stabilised pillared layered clay obtained by reacting a smectite-type clay with an aqueous solution of a polymeric cationic hydroxy inorganic metal complex.

28. A process for the catalysed dealkylation of an alkyl aromatic hydrocarbon comprising reacting in the liquid phase in an alkylation zone an aromatic hydrocarbon with an alkylating agent selected from $C_2$ to $C_{10}$ alcohols and olefins under alkylation conditions in the presence as catalyst of a cation-exchangeable layered clay or stabilised pillared layered clay to form a product comprising unreacted aromatic hydrocarbon, monoalkylated aromatic hydrocarbon and polyalkylated aromatic hydrocarbon, recovering at least some of the monoalkylated aromatic hydrocarbon from the product.

29. A process according to claim 28, further comprising
recycling at least part of the remainder of the product comprising aromatic hydrocarbon, any monoalkylated aromatic hydrocarbon and polyalkylated aromatic hydrocarbon with the feed to the alkylation zone.

30. A process according to claim 28, further comprising
passing at least part of the remainder of the product comprising aromatic hydrocarbon, any monoalkylated aromatic hydrocarbon and polyalkylated aromatic hydrocarbon, to a dealkylation zone wherein it is contacted with a catalyst comprising a cation-exchangeable layered clay or stabilised pillared interlayered clay under dealkylation conditions and recovering therefrom a monoalkylated aromatic hydrocarbon.

31. A process according to claim 28, further comprising
separating the aromatic hydrocarbon from the polyalkylated aromatic hydrocarbon, passing the polyalkylated aromatic hydrocarbon to a dealkylation zone wherein it is contacted with a cation-exchangeable layered clay or stabilised pillared layered clay catalyst under dealkylation conditions and recovering a monoalkylated aromatic hydrocarbon therefrom.

32. A process for the catalysed dealkylation of an alkyl aromatic hydrocarbon comprising in a first step reacting in the liquid phase in an alkylation zone under alkylation conditions an aromatic hydrocarbon with an alkylating agent selected from $C_2$ to $C_{10}$ alcohols and olefins, in the presence of a catalyst comprising a cation-exchangeable layered clay or stabilised pillared layered clay to form an alkylation product comprising unreacted aromatic hydrocarbon, monoalkylated aromatic hydrocarbon, polyalkylated aromatic hydrocarbon and in a separate second step reacting the alkylation product from the first step in a dealkylation zone under dealkylation conditions in the presence of a catalyst comprising a cation-exchangeable layered clay or stabilised pillared layered clay so as to increase the proportion of the monoalkylated aromatic hydrocarbon in the alkylation product, recovering at least some of the monoalkylated aromatic hydrocarbon and thereafter recycling at least part of the remainder of the product comprising aromatic hydrocarbon, any monoalkylated aromatic hydrocarbon, and polyalkylated aromatic hydrocarbon.

33. A process according to claim 32 wherein the alkylation conditions are such that substantial dealkylation is avoided in the alkylation zone and the dealkylation conditions are such that dealkylation is favoured in the dealkylation zone.

34. A process according to claim 32, wherein the recycling of at least part of the remainder of the product is with the feed to the dealkylation zone.

35. A process according to claim 32, wherein the recycling of at least part of the remainder of the product is with the feed to the alkylation zone.

36. A process according to claim 32, wherein the recycling of at least part of the remainder of the product is
(a) with the feed to the dealkylation zone, and
(b) with the feed to the alkylation zone.

* * * * *

UNITED STATES PATENT AND TRADEMARK OFFICE
CERTIFICATE OF CORRECTION

PATENT NO. :   4,599,470

DATED      :   July 8, 1986

INVENTOR(S) :  REGINALD GREGORY et al

It is certified that error appears in the above-identified patent and that said Letters Patent is hereby corrected as shown below:

Col. 8, line 35,   "(100 ml)" should read --(1100 ml)--

Signed and Sealed this

Twenty-third Day of December, 1986

Attest:

DONALD J. QUIGG

Attesting Officer            Commissioner of Patents and Trademarks